United States Patent [19]

Okamoto et al.

[11] 4,173,398
[45] Nov. 6, 1979

[54] OPTICAL SYSTEM FOR OBJECTIVE EYE-EXAMINATION

[75] Inventors: Ikuzo Okamoto, Tamagawa; Osamu Shindo, Tokyo, both of Japan

[73] Assignee: Asahi Kogaku Kogyo Kabushiki Kaisha, Tokyo, Japan

[21] Appl. No.: 885,051

[22] Filed: Mar. 9, 1978

[30] Foreign Application Priority Data

Mar. 11, 1977 [JP] Japan ............................. 52-26685

[51] Int. Cl.² ............................................. A61B 3/10
[52] U.S. Cl. ........................................ 351/9; 250/200; 351/13; 351/14; 351/15; 356/126; 356/128
[58] Field of Search ............. 351/6, 9, 14, 15, 13; 250/200; 356/126, 128

[56] References Cited

U.S. PATENT DOCUMENTS

| | | | |
|---|---|---|---|
| 3,602,580 | 8/1971 | Samuels | 351/9 X |
| 3,819,256 | 6/1974 | Bellows et al. | 351/13 X |
| 4,021,102 | 5/1977 | Iizuka | 351/6 X |

OTHER PUBLICATIONS

F. W. Campbell et al., "High Speed Infrared Optometry," JOSA, vol. 49, No. 3, pp. 268–272, Mar. 1959.

*Primary Examiner*—Paul A. Sacher
*Attorney, Agent, or Firm*—Sughrue, Rothwell, Mion, Zinn and Macpeak

[57] ABSTRACT

An objective eye examination apparatus generates rotating pencil rays of infrared light and focuses one of them on the eye pupil via an adjustable wedge reflector 55, 57 for varying the effective length of the optical axis. Light reflected back by the retina and returned into the optical system is passed through an image rotator 41 onto a quadrant photocell 43. The wedge reflector is adjusted until the differential outputs from the photocell reach a desired value, whereby the necessary reflector adjustment is indicative of refractive power. Unfocusable fogging light is also introduced into the eye via a dichroic mirror 39, and a further photocell 35 is disposed to receive light reflected back from the cornea only when the eye is properly positioned and open.

5 Claims, 4 Drawing Figures

OUTPUT = (A+B)−(C+D)

A-1

A-2

A-3

B-1

B-2

B-3

C-1

C-2

C-3

$x = (A+B) - (C+B)$
$y = (B+D) - (A+C)$

OPTICAL SYSTEM FOR OBJECTIVE EYE-EXAMINATION

BACKGROUND OF THE INVENTION

This invention relates to an optical system for an automatic objective eye-examining apparatus which can measure the refractive power of an eye using invisible infrared rays.

As described in applicant's Japanese Patent Application No. 51-120636, systems for measuring the refractive power of an eye are generally of the subjective type or the objective type. The subjective type system includes the conventional vision testers which have been widely used for a long time, the Humphrey Vision Analyzer recently developed by Humphrey Instruments Inc., (USA) etc. It is difficult to obtain accurate measurements with subjective type apparatuses, particularly when older persons or children are being examined, as they must answer various questions asked by the examiner during the refractive power measuring operation.

On the other hand, although some automatic objective type eye-examining apparatuses can measure the eye refractive power without any subjective response of the person being examined, they are inconvenient to use owing to a large movable focusing system, the complex step switching of different meridian planes, etc.

SUMMARY OF THE INVENTION

It is therefore a principle object of the invention to provide a simple and high precision optical system for measuring the refractive power of an eye which improves upon the apparatus disclosed in the aforementioned Japanese Patent Application. Such improved apparatus incorporates a fogging optical system for rendering the focal control power of the eye inoperable during the refractive power measuring operation, whereby an independent fogging system is unnecessary and most of the optical noise generated by a light transfer system for irradiating the retina is eliminated.

Briefly, and in accordance with the present invention, an objective eye examination apparatus generates rotating pencil rays of infrared light and focuses one of them on the eye pupil via an adjustable wedge reflector for varying the effective length of the optical axis. Light reflected back by the retina and returned into the optical system is passed through an image rotator onto a quadrant photocell. The wedge reflector is adjusted until the differential outputs from the photocell reach a desired value, whereby the necessary reflector adjustment is indicative of refractive power. Unfocusable fogging light is also introduced into the eye via a dichroic mirror, and a further photocell is disposed to receive light reflected back from the cornea only when the eye is properly positioned and open.

DETAILED DESCRIPTION OF THE PREFERRED EMBODIMENT

Figure 1:
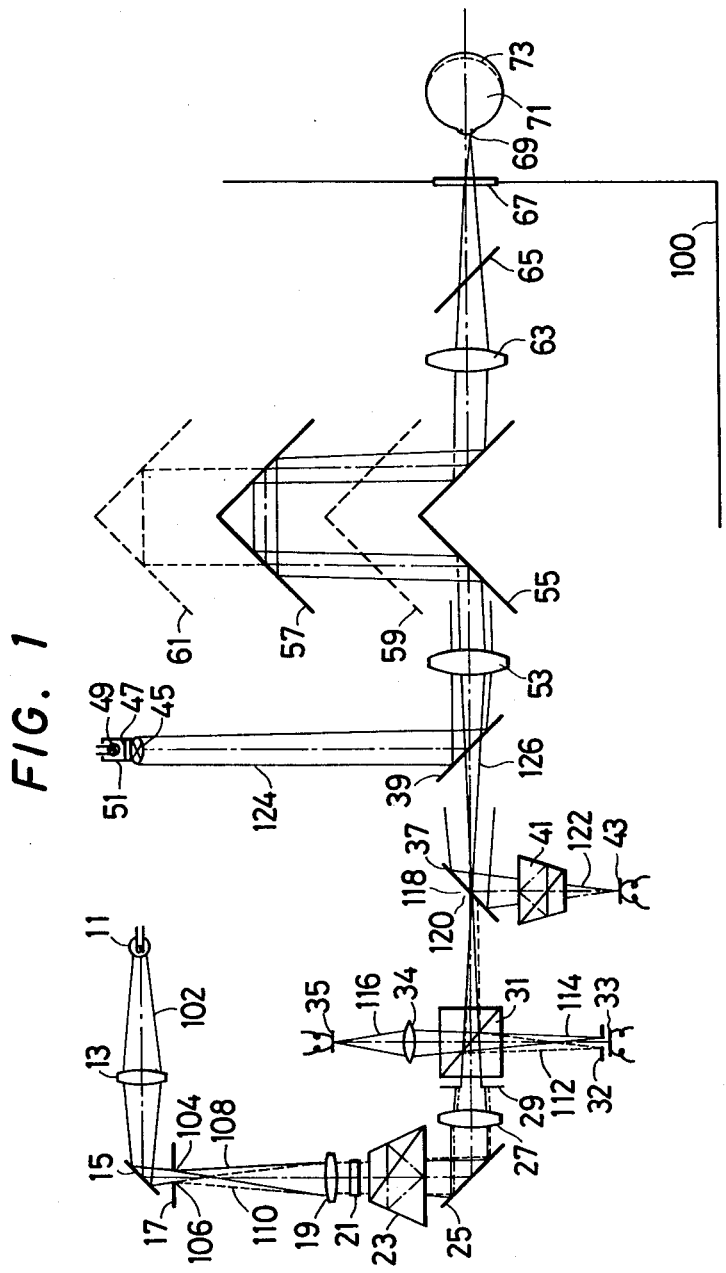
FIG. 1 shows a simplified schematic diagram of an optical eye examination system constructed in accordance with the invention.

In the drawings, FIG. 1 shows a complete optical system for an automatic objective eye-examination apparatus 100.

A light source 11 emits light flux 102 which is condensed by a lens 13, reflected by a mirror 15, and focused into an image on a plate 17 having two pinholes 104 and 106 therein slightly displaced from the optical axis. The two pinholes provide two pencil rays 108 and 110 paralleled by a collimator lens 19 focused on the pinhole plate 17. The parallel pencil rays 108 and 110 then pass through a filter 21 transparent to infrared rays, and are rotated by a high velocity image rotator 23. A mirror 25 reflects the pencil rays through a condenser lens 27, which focuses them into an image on an angularly disposed, centrally open reflector 37 through an aperture plate 29 and a beam splitter 31. The pencil ray 108 emitted from pinhole 104 closest to the optical axis is focused in the opening of mirror 37 while the other pencil ray 110 from the pinhole 106 more remote from the optical axis is focused outside of the mirror opening during the rotation of the pencil rays about the optical axis by the image rotator 23.

While the spot 118 of infrared rays which rotates around outside the periphery of the mirror opening is reflected away, the spot 120 which rotates in the opening forms a pencil ray 126 which passes through a dichroic mirror 39 disposed at an angle of 45 degrees to the optical axis. This mirror is transparent to infrared rays but reflects visible light, and passes the pencil ray to a collimator lens 53. The parallel pencil ray 126 is then reflected by a fixed 90 degree wedge-shaped mirror 55 disposed at an angle of 45 degrees to the optical axis, and return reflected by a pair of correspondingly wedge-shaped mirrors 57 disposed at a variable distance from the mirror 55. The returned pencil ray is focused by an imaging lens 63, passes through a translucent mirror 65 and measuring window 67 for positioning the eye, and forms an image at a point on the pupil plane which is projected onto the retina 73.

Beam splitter 31 reflects a portion of the pencil rays 108 and 110 away from the optical axis and forms converging pencil rays 114 and 112, respectively. A slit 32 disposed just before a photocell 33 prevents the rotating pencil ray 114 from passing therethrough and provides a reference signal only when the rotating pencil ray 112 passes through the slit opening.

The pencil ray reflected by the cornea is returned back into the system, focused into an image adjacent the central opening of the angularly disposed reflector 37, and laterally reflected by the beam splitter 31 to be focused by a condenser lens 34 into an image on a photocell 35. When the eye being examined is correctly positioned, the rays reflected from the cornea are always projected on photocell 35 which thus provides a constant output signal, whereby it is possible to detect any blinking or displacement of the eye from the optical axis and thus prevent incorrect measurements.

Figure 2:
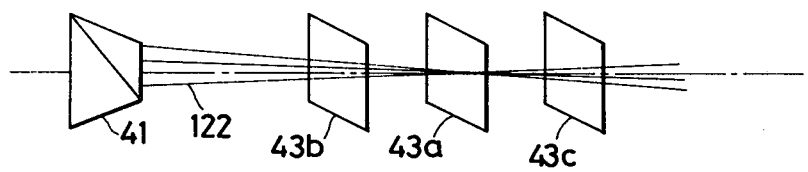
FIG. 2 shows the imaging conditions at the level of a quadrant photocell detector.
Figure 3:
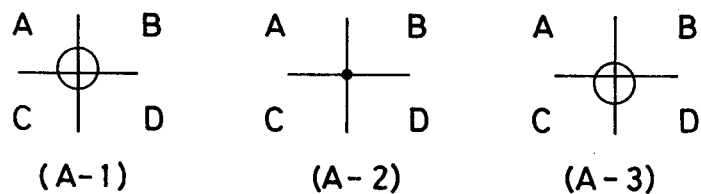
FIG. 3 shows the different focal conditions, output signals and reference pulses for hyperopia, emmetropia and myopia.
Figure 3:
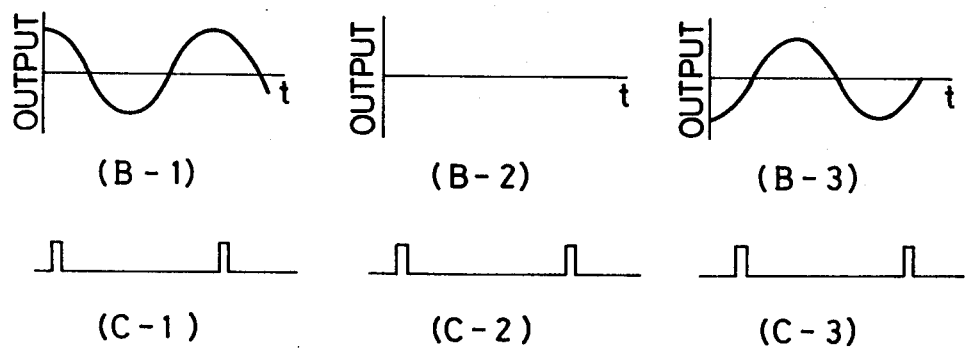

Abnormality of eye refraction is caused either by the spherical power of the eye alone, or in combination with the cylinder power of the eye; when only the spherical or surface power is involved the rays 122 reflected from the retina 73 are focused on a differential or quadrant photocell 43 as shown in FIGS. 2 and 3. When the movable reflector 57 is in its zero position and pencil ray 122 is focused at the center plane 43a of the photocell as shown in FIG. 2, the eyesight is emmetropic; when pencil ray 122 is focused at plane 43b to the rear of the photocell, hyperopia is indicated; and when pencil ray 122 is focused at plane 43c forward of the photocell, shortsightedness is indicated.

In FIG. 3, A-1, A-2 and A-3 illustrate the imaging conditions when the eyesight is hyperopic, emmetropic and myopic, respectively; B-1, B-2 and B-3 show the photocell outputs produced by the quadrant combination of (A+B)-(C+D); and C-1, C-2 and C-3 show clock signals for referencing the output signals B-1, B-2 and B-3, respectively. That is, the apparatus processing or output signal is derived each time a reference pulse is generated. Since a hyperopic eye generates the signal B-1 in FIG. 3 and this provides a positive output signal, the latter may be brought to zero, as at B-2 in FIG. 3, by displacing the movable reflector 57 toward the position shown by the dotted line 61. Similarly, with a shortsighted eye the negative output signal may be brought to zero by displacing the reflector 57 toward the dotted line position 59. The necessary zeroing displacements of mirror 57 indicate the degree of abnormality of the refractive power of the eye. The reflector 57 may be manually adjusted or servo-controlled as the output signals vary depending on the sight conditions, i.e. either hyperopia, emmetropia, or myopia.

Figure 4:
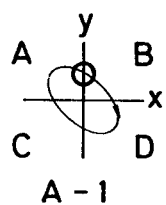
FIG. 4 shows the different focal conditions on and output signals from a quadrant photocell when refractive abnormalities which include cylinder power abnormalities are present.
Figure 4:
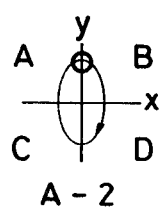
Figure 4:
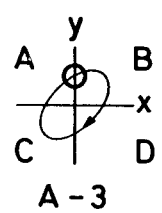
Figure 4:
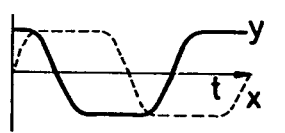
Figure 4:
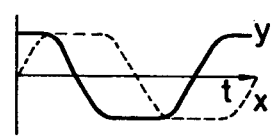
Figure 4:
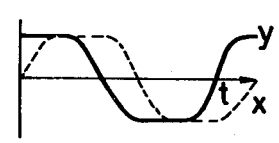
Figure 4:
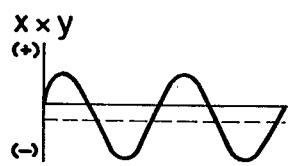
Figure 4:
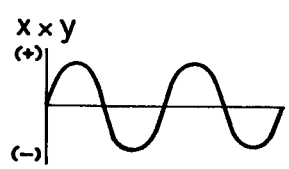
Figure 4:
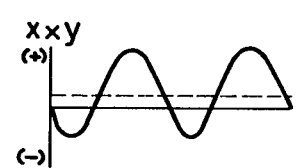

In FIG. 4 an alternative eye examination method will be described for the cases when the spherical power and cylinder power measurements are combined, or when only the cylinder power measurement is made. In the figure, A-1 shows the focal condition of pencil ray 122 on the quadrant photocell 43 when the cylinder axis is inclined 45 degrees to the optical sub-axis, whereby the pencil ray describes an elliptical orbit. B-1 in FIG. 4 shows the output signals derived from condition A-1 wherein x and y represent the signal combinations (A+B) - (C+D) and (B+D) - (A+C), respectively. C-1 in FIG. 4 shows the combined output signal x×y, the mean thereof being negative. This signal initiates the rotational drive of image rotator 41 to bring the cylinder axis in coincidence with the photocell axis as shown at A-2 in FIG. 4, which produces the output signals shown at B-2 and C-2. When the axes coincide with each other refractive power may be determined along the x and y directions using the same method for determining the spherical refractive power as described above in connection with FIG. 3, and the difference between the two resultants then represents the cylinder power. The cylinder axis can also be determined by detecting the rotational angle of image rotator 41 necessary to bring the mean output of x×y to zero. A-3 in FIG. 4 shows the focal condition when the cylinder axis is inclined by an angle of 135 degrees, and the corresponding output signals x and y and x×y are shown at B-3 and C-3 in FIG. 4, respectively, the mean value thereof being positive. Accordingly, the detection of the cylinder axis may easily be servo-controlled since the inclination of the axis to the ordinate y can be very simply determined by detecting the mean output of x×y on the abscissa x.

Fogging means indispensable to eliminating any natural eye adjustment effort during the examination may be directly incorporated into the optical refractive power measurement system according to the invention. Fogging means 51 comprising a fogging light source 49, a monochrome filter 47 and a fogging chart 45 is disposed in a position slightly displaced from the equivalent optical distance of aperture plate 29 relative to the collimator lens 53. Pencil Ray 124 emitted from the fogging chart 45 is reflected by dichroic mirror 39 and introduced in the optical refractive power measurement system so as to be projected on the eye retina 73. As the displacement of the movable reflector 57 depends on the refractive power of the eye being examined, the rays projected by the slightly displaced fogging chart 45 cannot become focused on the retina regardless of the refractive abnormalities of the eye. That is, with such proper fogging the person being examined always observes a hazy or misty image.

What is claimed is:

1. An optical apparatus for objective eye examination, comprising:
   (a) means for generating two rotating pencil rays of infrared light each slightly displaced by different amounts from an optical axis,
   (b) reflector means having a central opening therein angularly disposed on the optical axis,
   (c) means for focusing said pencil rays in the vicinity of said reflector means opening,
   (d) a dichroic mirror disposed on the optical axis beyond the reflector means for reflecting visible light and passing infrared light,
   (e) a collimator lens disposed on the optical axis for paralleling any infrared light passed through the dichroic mirror,
   (f) a fixed 90° wedge-shaped outward reflector angularly disposed on the optical axis,
   (g) a movable 90° wedge-shaped inward reflector cooperable with the fixed reflector for varying the effective length of the optical axis,
   (h) a focusing lens for forming an infrared light image on the pupil of an eye being examined, said image being projected on the eye retina and reflected thereby back along the optical axis,
   (i) an image rotator disposed to receive returned infrared light reflected thereon by said reflector means,
   (j) a quadrant photodetector disposed to receive infrared light from said image rotator, and
   (k) means for generating differential output signals from said photodetector outputs, whereby said movable reflector may be moved until said differential output signals reach an optimum value, the necessary degree of such movement being indicative of the refractive power of the eye.

2. An optical apparatus as defined in claim 1, further comprising means responsive to said differential output signals for automatically moving said movable reflector until said output signals reach said optimum value.

3. An optical apparatus as defined in claims 1 or 2, wherein said pencil ray generating means comprises:
   (a) an incandescent light source,
   (b) a plate member having two pinholes therein each slightly displaced from the optical axis by different amounts,
   (c) means for focusing incandescent light from said source on said plate member,
   (d) a collimating lens disposed on the optical axis at a distance from the plate member equal to its focal length,
   (e) an infrared light filter disposed on the optical axis following said collimator lens, and (f) an image rotator disposed on the optical axis following the infrared filter, and wherein said pencil ray focusing means comprises:
(a) a focusing lens disposed on the optical axis following the image rotator,
(b) a centrally apertured plate member disposed on the optical axis following the focusing lens, and
(c) a beam splitter disposed on the optical axis following the apertured plate member.

4. An optical apparatus as defined in claims 1 or 2, further comprising:
(a) a beam splitter disposed on the optical axis ahead of said centrally open reflector means, and
(b) a photodetector disposed to receive infrared light returned through said central opening and reflected thereon by said beam splitter, whereby the output signal from said photodetector indicates the proper positioning of the eye being examined and detects any blinking thereof.

5. An optical apparatus as defined in claims 1 or 2, further comprising:
(a) a source of visible light, and
(b) a fogging member disposed between said light source and said dichroic mirror at an optical distance from the collimator lens unequal to the focal length thereof, whereby fogged light from said source is reflected into the infrared light path to fog the eye being examined.

* * * * *